United States Patent [19]
Bramley et al.

[11] Patent Number: 5,850,354
[45] Date of Patent: Dec. 15, 1998

[54] CALIBRATION METHOD FOR NDIR EQUIPMENT AND CALIBRATION APPARATUS

[75] Inventors: Paul Bramley; Richard Dennis, both of Edinburgh, Scotland; Christer Helenelund, Porvoon, Finland

[73] Assignee: Vaisala Oy, Helsinki, Finland

[21] Appl. No.: 620,610

[22] Filed: Mar. 22, 1996

[30] Foreign Application Priority Data

Mar. 22, 1995 [FI] Finland ..................................... 951339

[51] Int. Cl.⁶ ................................................. G01N 21/61
[52] U.S. Cl. ............................... 364/571.01; 364/571.05; 250/252.1; 73/1.03; 73/1.06
[58] Field of Search ..................................... 364/496, 498, 364/497, 499, 571.01, 571.02, 571.05, 571.04; 73/1 G, 1 R, 1.03, 1.06; 250/252.1 A, 343, 345, 341.5; 356/243

[56] References Cited

U.S. PATENT DOCUMENTS

| | | |
|---|---|---|
| 3,369,405 | 2/1968 | Galegar . |
| 4,825,683 | 5/1989 | Takami et al. ............................. 73/1 G |
| 5,072,416 | 12/1991 | Francisco et al. ................. 364/571.01 |
| 5,077,469 | 12/1991 | Fabinski et al. ......................... 250/345 |
| 5,184,017 | 2/1993 | Tury et al. .................... 250/252.1 A X |
| 5,243,546 | 9/1993 | Maggard ............................. 364/571.02 |
| 5,292,280 | 3/1994 | Janu et al. ................................ 454/229 |
| 5,321,638 | 6/1994 | Witney ........................... 364/571.01 X |
| 5,459,677 | 10/1995 | Kowalski et al. .................. 364/571.02 |
| 5,559,728 | 9/1996 | Kowalski et al. ............ 250/252.1 A X |

FOREIGN PATENT DOCUMENTS

| | | |
|---|---|---|
| 600711 | 11/1993 | European Pat. Off. . |
| 850320 | 7/1986 | Finland . |
| 74353 | 9/1987 | Finland . |
| 91021 | 5/1990 | Finland . |
| 89210 | 12/1991 | Finland . |
| 59-173734 | 3/1983 | Japan . |

*Primary Examiner*—Melanie Kemper

[57] ABSTRACT

A method and apparatus for calibrating an NDIR gas analyzer is provided. According to the method, the apparatus under calibration is calibrated with the help of a reference apparatus under controlled conditions. The reference apparatus is a laboratory-calibrated NDIR measurement apparatus in an arrangement based on circulating ambient air via both a measurement chamber of the measurement apparatus under calibration and measurement chamber of the laboratory-calibrated measurement apparatus. Adjusting the reading of a display, or alternatively, an output signal of the measurement apparatus under calibration to be equal to the reading of the display, or the output signal, respectively, of the reference apparatus is performed by a control device of the measurement apparatus.

8 Claims, 4 Drawing Sheets

CALIBRATION METHOD FOR NDIR EQUIPMENT AND CALIBRATION APPARATUS

FIELD OF THE INVENTION

The invention relates to a calibration method and apparatus for an NDIR gas analyzer.

BACKGROUND OF THE INVENTION

Nondispersive infra-red (NDIR) measurement equipment of the lower price class have typically had a construction in which the output signal exhibits a drifting tendency with the aging of the equipment. The technology of NDIR equipment is elucidated at the basic level in, e.g., the Japanese patent publication 59-173734. According to conventional methods, it has usually been necessary to take the measurement equipment to a laboratory for calibration, whereby the measured object has been left unmonitored for the duration of the calibration operation. Such a laboratory calibration is an expensive and time-consuming operation which, however, must be repeated at certain intervals to maintain desired measurement accuracy. The above problems have been particularly annoying in air-conditioning applications where the NDIR equipment has been used for monitoring of the carbon dioxide concentration of the circulating air, and disturbance to the function of the air-conditioning system has been caused by the drift of the measurement equipment.

SUMMARY OF THE INVENTION

It is an object of the present invention to overcome the drawbacks of the above-described techniques and to achieve an entirely novel calibration method and apparatus.

The invention is based on performing the calibration of the NDIR equipment by connecting a laboratory-calibrated NDIR measurement equipment in parallel with the equipment to be calibrated and then circulating the ambient gas so that the gas flowing via the equipment to be calibrated is subsequently taken to the sample chamber of the reference measurement equipment precalibrated under laboratory conditions.

More specifically, a method according to a first embodiment of the method includes a calibration method for an NDIR gas analyzer comprising the steps of providing a measurement apparatus for calibrating the measurement apparatus including a measurement chamber, providing a reference laboratory calibrated NDIR measurement apparatus for aiding calibration of the measurement apparatus, the NDIR measurement apparatus including a measurement chamber, connecting operatively the measurement apparatus and the reference laboratory calibrated NDIR measurement apparatus, and adjusting a reading of a display or alternatively, an output signal of the measurement apparatus to be equal to a reading of a display or output signal of the reference laboratory calibrated NDIR measurement apparatus.

Furthermore, an apparatus according to a first embodiment of the apparatus includes an apparatus for calibrating an NDIR gas analyzer, said apparatus comprising a reference apparatus for the calibration of a measurement apparatus to be calibrated, the reference apparatus is a laboratory-calibrated NDIR measurement apparatus, which includes a measurement chamber, said measurement apparatus includes a measurement chamber, and means for transferring ambient air via the measurement chamber of the measurement apparatus and the measurement chamber of the reference apparatus.

The invention offers significant benefits. No separate calibration gas mixture or laboratory calibration with pressure and temperature compensation is required in the field calibration procedure. Such separate calibration gas mixtures are expensive, awkward to use, and moreover, the omission of pressure and temperature compensation in a conventional calibration procedure would involve excessively large uncertainty factors if the calibration would be carried out in the form of a conventional field calibration. The method according to the invention facilitates simple, quick and cost-effective field calibration, whereby the measurement equipment itself need not be disconnected from the control system for the duration of the calibration operation.

BRIEF DESCRIPTION OF DRAWINGS

In the following, the invention will be examined in more detail by means of exemplifying embodiments with reference to the attached drawings, in which:

With reference to FIG. 1, a calibration arrangement according to the invention principally comprises four blocks, namely an NDIR measurement apparatus 1 to be calibrated, another NDIR measurement apparatus 2 calibrated in a laboratory, the electronics section 21 of the apparatus to be calibrated and the electronics section 20 of the reference apparatus. In the context of this invention, the term laboratory calibration refers to a procedure in which the display reading or output signal of the measurement apparatus is adjusted at known temperature and pressure to the correct value using at least two different calibration gas mixtures having different and exactly known concentrations of their components. For carbon dioxide measurements, the calibration gas mixtures typically employed include nitrogen to establish the zero point of the apparatus, while the other concentration point to be calibrated typically is the upper limit of the measurement range, e.g., 2000 ppm carbon dioxide.

Figure 1:
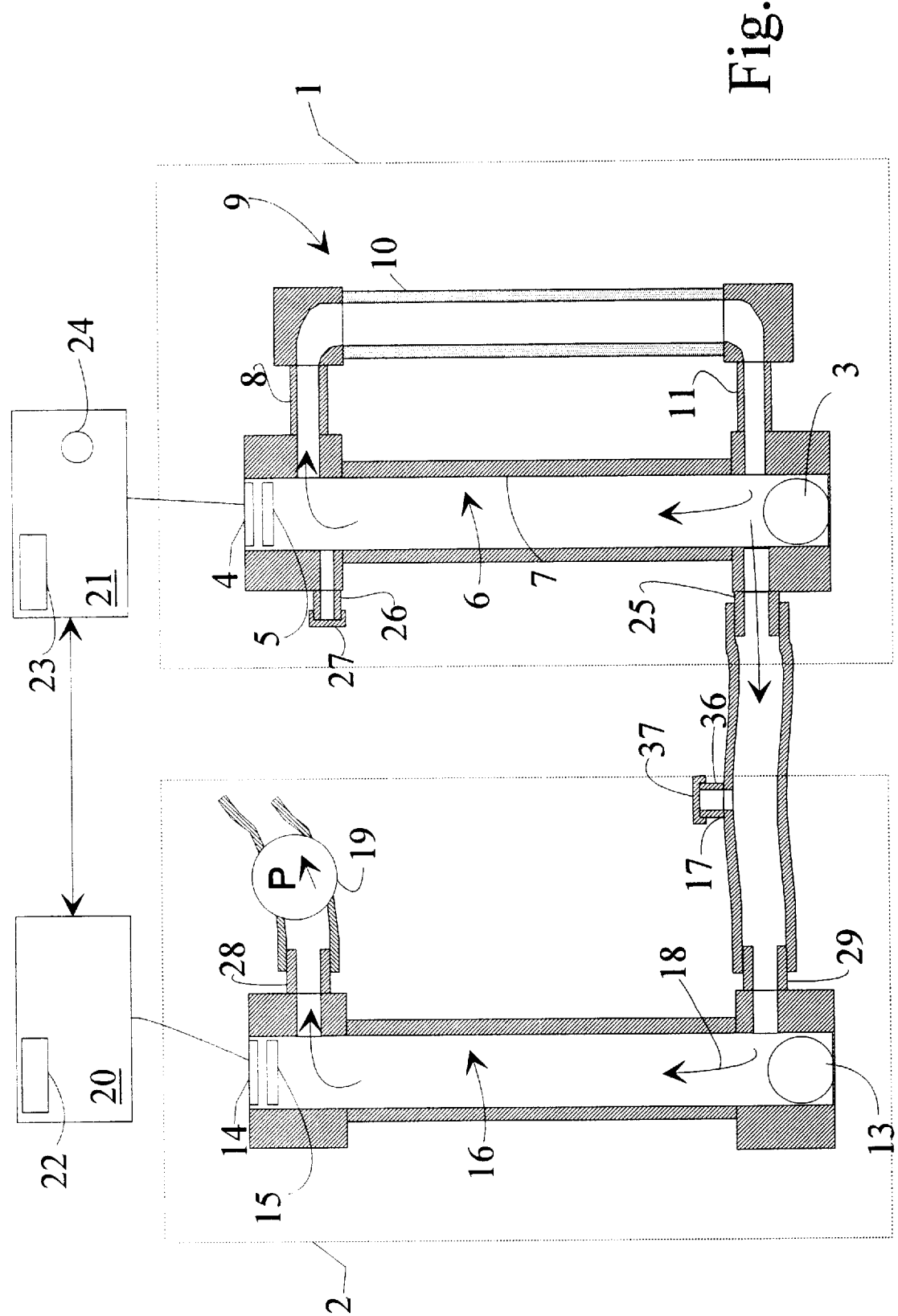
FIG. 1 is a schematic diagram of a calibration arrangement according to the invention.

Typically, an NDIR measurement apparatus incorporates a light source 3 adapted to emit infra-red radiation to a measurement chamber 6. The radiation passing through the measurement chamber is filtered by means of a bandpass filter 5 and detected by means of a detector 4. The entity formed by the light source 3, the measurement chamber 6, the bandpass filter 5 and the detector 4 might also be called an optical calibration bench. The measurement result obtained therefrom is processed in an electronics unit 21 whose output signal is proportional to the gas concentration and may indicated on the display 23 as the gas concentration reading if so desired. In the illustrated embodiment the gas is passed by thermally-induced flow to the measurement chamber 6 from a bypass flow pipe 9 which is connected to the optical calibration bench by means of an inlet pipe 11 and an outlet pipe 8. The bypass flow pipe 9 has a gas-permeable pipe section 10 through which the gas to be measured is admitted from the ambient atmosphere surrounding the measurement apparatus to the gas circulation of the apparatus, and therefrom, to the measurement chamber 6. In an apparatus of the lower price class, such a gas circulation is implemented by means of thermally-induced flow caused by the heat emitted by a light source 3. Separate pumps may also be used for circulating the gas.

According to the invention, the measurement apparatus to be calibrated is provided with a second outlet pipe 25 which is connected by a hose 17 to the optical calibration bench of the reference apparatus 2. The reference apparatus 2 is precalibrated under laboratory conditions to provide an accurate concentration reading on the display 22 of the reference apparatus. Similarly to the apparatus 1, also the reference apparatus comprises a light source 13, a measurement chamber 16, a bandpass filter 15 and a detector 14 which is connected to an electronics unit 20 whose output is taken to a gas concentration display 22. To the outlet pipe 28, or alternatively, the inlet pipe 29 of the reference apparatus 2 is connected a suction pipe 19 adapted to pump gas into the reference apparatus 1 from the ambient atmosphere thus feeding the measurement chamber 16 of the reference apparatus 2 with essentially the same ambient gas mixture as that of the other apparatus. Owing to the long time constant of the measurement due to the finite length of the gas flow channel, the ambient gas concentration must be assumed to stay essentially constant during the calibration measurement procedure. Provided that the response time of both measurement chambers and electronics units is the same and the flow rate is known, also a variable gas concentration may be used in the calibration measurement. Then, the comparison of the measurement values is performed by, e.g., correcting the readings by a known flow delay, or alternatively, the measurement curves are optimally matched using computational methods.

During the calibration operation, the display readings, or alternatively, the output signals of the electronics units 20 and 21 are compared, after which the reading of the display 23, or alternatively, the output signal of the measurement apparatus 1 under calibration is adjusted by a calibration control 24 equal to the reading of the display 22 or output signal, respectively, of the reference apparatus 2. The calibration control 24 may in practice be, e.g., a potentiometer in the electronics unit 21. Alternatively, the calibration operation may be automated, whereby the electronics unit 21 of the apparatus 1 under calibration is provided with a connector for the signals of the reference apparatus 2, and the calibrating signal is transferred under the control of a processor from the reference apparatus 20 to the electronics unit 21.

The system according to the invention described above is for calibration at a single point of concentration. Also a simple arrangement for two-point calibration is feasible therein that to the connector 26 of the apparatus 1, or alternatively, to a T-connector 36 of the hose 17 is fed a reference gas mixture having its concentration approximately known. In the case of carbon dioxide, such reference gas can be formed by, e.g., blowing into a balloon or similar container a preset amount of expiration air, exhaust gas or other gas containing excess amounts of carbon dioxide from combustion and then filling the remaining volume of the balloon by air pumped from the ambient atmosphere. The balloon thus filled is discharged via the connector 26 to the measurement chamber 6, wherefrom the pump of the calibration bench pumps it to the measurement chamber 16 of the reference apparatus 2. The calibration inlet connector 26 is normally covered by an air-tight protective cap 27. Correspondingly, the T-connector 36 is normally covered by a similar protective cap 37.

The pump 19 is conventionally a suction pump, while the use of a positive-head pump forming an overpressure may also be contemplated within the scope of the invention.

Figure 2:
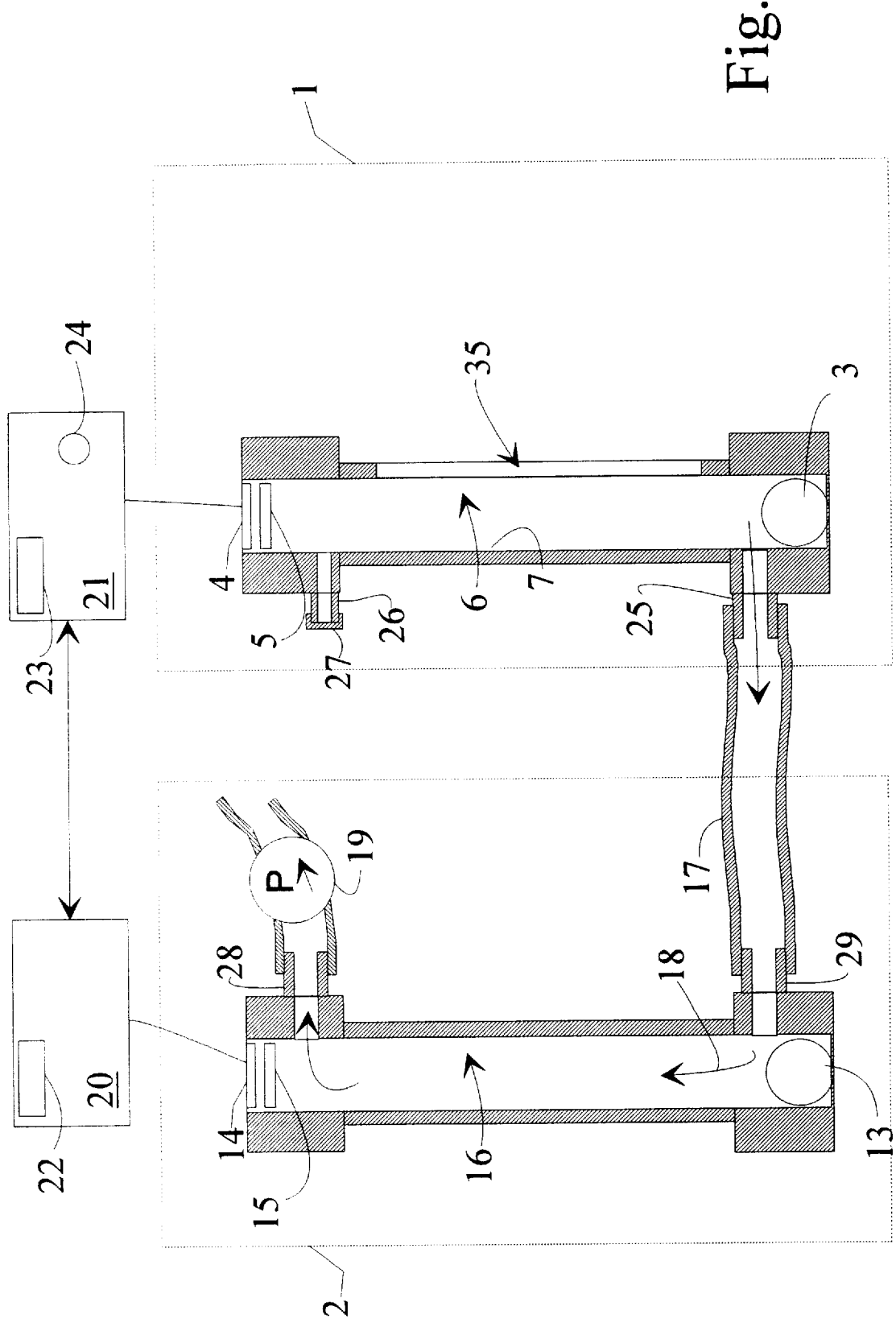
FIG. 2 is a schematic diagram of another calibration arrangement according to the invention.

With reference to FIG. 2, the NDIR measurement apparatus 1 to be calibrated can be provided with an oblong flow slit 35 equipped with a diffusion filter, whereby the bypass flow channel 9 illustrated in FIG. 1 is unnecessary.

Figure 3:
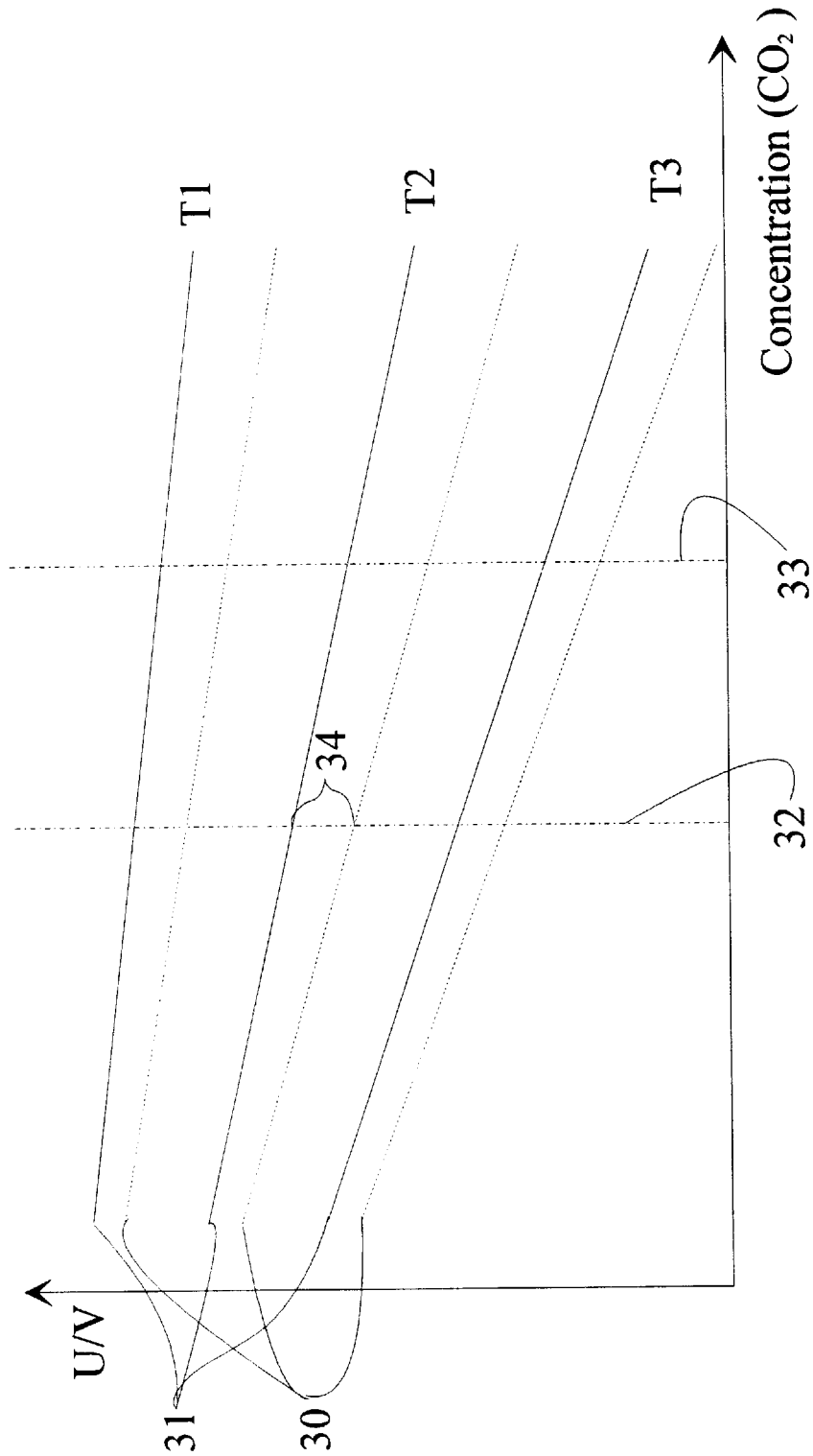
FIG. 3 is a graph of a typical output voltage-concentration curve family for NDIR equipment.

With reference to FIG. 3, the dependence of the detector output signal of an ideal NDIR measurement apparatus on the gas concentration is plotted in a graph. The vertical axis is the detector output voltage, while the horizontal axis is the gas concentration. The solid-line graphs 31 represent the calibrated output curves of the apparatus 2 shown in FIG. 1 at three different ambient temperatures or barometric pressures. The dotted-line graphs 30 represent the corresponding output curves of the apparatus 1 under calibration under three different ambient conditions. In the calibration operation according to the invention, the gas concentration may be assumed to be, e.g., at the level of line 32, while the temperature is T2 and the barometric pressure in both measurement chambers is essentially equal. For the procedure the level of gas concentration need not be known exactly, but rather, equal gas concentrations in both apparatuses 1 and 2 will suffice. When the ambient air is sucked by means of the pump 19 of FIG. 1 via the reference apparatus 2, the readings of both displays 22 and 23 should be equal. In the illustrated case the output voltage difference is equal to the line denoted by reference numeral 34 in the graph. The output voltage error is corrected by adjusting the potentiometer 24, or alternatively, transferring the correction factor in digital form provided that such a facility is implemented in the NDIR apparatus. Correspondingly, a two-point calibration may be performed in the above-described manner using the balloon technique from which another reference gas concentration 33 is obtained, whereby also the slope of the output curve of the measurement apparatus 1 under calibration can be corrected according to the slope T2 of the output curve of the precalibrated apparatus. If desired the balloon technique may be replaced by any other container filled with the reference gas under elevated or ambient pressure, and the flow may be arranged by means of a powered or manual pump.

Figure 4:
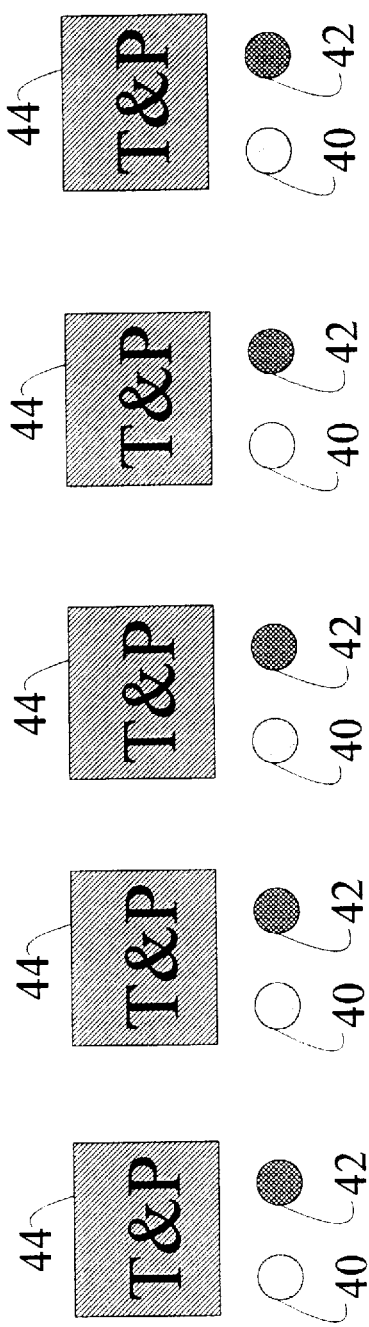
FIG. 4 is a schematic diagram of a conventional calibration arrangement.

With reference to FIG. 4, the calibration of five NDIR measurement apparatuses 44 according to conventional techniques have necessitated feeding each measurement apparatus with two reference gas mixtures 40 and 42 of exactly known concentration at known temperature and pressure. Because such unique conditions are difficult to achieve under field conditions, calibration by the prior-art techniques must generally be carried out in a laboratory or service facility.

Figure 5:
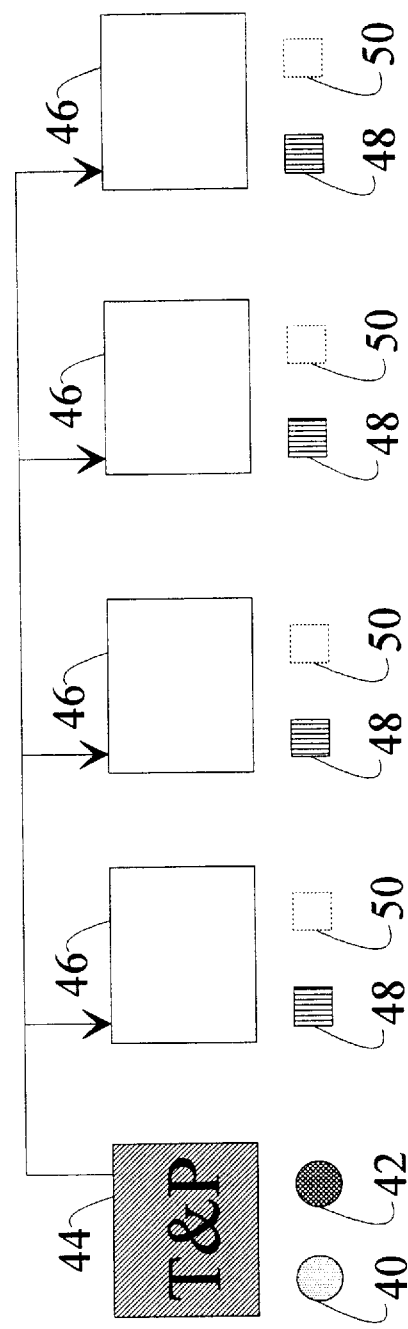
FIG. 5 is a schematic diagram of a calibration arrangement according to the invention.

With reference to FIG. 5, the arrangement shown therein achieves under field conditions almost the same accuracy as the conventional technique using only one laboratory-calibrated measurement apparatus 44 employing ambient air 48, or alternatively, additionally using another reference gas 50. According to the invention, the concentrations of the reference gases 48 and 50 need not be know accurately beforehand. Furthermore, the pressure and temperature (T&P) need not be known during the calibration.

Besides carbon dioxide, the calibration arrangement according to the invention is applicable to, i.a., absolute humidity, carbon monoxide, hydrocarbons such as methane or ethylene for instance, and nitrous oxide.

We claim:

1. An apparatus, said apparatus comprising:
   a measurement apparatus having a measurement chamber;
   a reference apparatus for calibration of the measurement apparatus the reference apparatus being a laboratory-calibrated NDIR measurement apparatus, which includes a measurement chamber, and means for transferring ambient air via the measurement chamber of the measurement apparatus and the measurement chamber of the reference apparatus, and means for adjusting a display or alternatively an output signal of the measurement apparatus to be equal to a reading of a display or an output signal of the reference apparatus, so that the measurement apparatus is calibrated.

2. The apparatus as defined in claim 1, wherein said reference apparatus includes means for directly forming a value of the difference between measurement results of the reference apparatus and the measurement apparatus.

3. The apparatus as defined in claim 1, said reference apparatus includes means for transferring a correction factor based on a difference of signals under the control of a processor directly to the measurement apparatus.

4. The apparatus as defined in claim 2, wherein said reference apparatus includes means for transferring a correction factor based on a difference of signals under the control of a processor directly to the apparatus.

5. The apparatus as defined in claim 1, wherein the measurement apparatus includes a bypass channel operatively connected to the measurement chamber of the measurement apparatus.

6. The apparatus as defined in claim 5, wherein the bypass channel has a gas-permeable pipe section.

7. The apparatus as defined in claim 1, wherein the reference apparatus includes an electronic unit with signal outputs and said measurement apparatus includes an electronic unit.

8. The apparatus as defined in claim 1, wherein the measurement chamber of the measurement apparatus includes an oblong slit and a filter.

* * * * *